United States Patent [19]

Pál et al.

[11] Patent Number: 4,617,830
[45] Date of Patent: Oct. 21, 1986

[54] METHOD AND APPARATUS FOR CHECKING HETEROGENEOUS TRANSFORMATION PROCESS OF DIFFUSING KINETICS IN TURBULENT LIQUID FLOW

[76] Inventors: Gábor Pál, Hómező u.64, 1221 Budapest; Gábor Endröczi, Veres Pálné u. 14, 1053 Budapest; György Hollós, Frankel Leo u.23, 1023 Budapest; Gábor Nagy, Árpád u. 64; Gábor Szönyi, Stadion u. 23, both of 3534 Miskolc; Bódi László, Gyula u. 38, 3532 Miskolc; Zoltán Balázs, Kóris Kálmán u. 17, 3530 Miskolc, all of Hungary

[21] Appl. No.: 731,212

[22] Filed: May 7, 1985

[51] Int. Cl.$^4$ .................................................. G01N 29/00
[52] U.S. Cl. .................................... 73/590; 73/61.1 R
[58] Field of Search .................... 73/590, 61 R, 61.1 R

[56] References Cited

U.S. PATENT DOCUMENTS 3,548,640 12/1970 Deason et al. ........................ 73/590

*Primary Examiner*—Stephen A. Kreitman
*Attorney, Agent, or Firm*—Sughrue, Mion, Zinn, Macpeak and Seas

[57] ABSTRACT

A method and apparatus for checking a heterogeneous transformation process of diffusion kinetics taking in a turbulent flow of a liquid, whereby the real-time checking or control of the processes is possible. The method involves the steps of detecting acoustic vibrations caused by oscillations of bubbles present in the turbulent flow of liquid, producing an electric signal reflecting the spectral compostion of the detected signal, and forming therefrom a measure signal reflecting the relative instantaneous value of the turbulent diffusion coefficient of the flowing liquid. The apparatus comprises a series circuit including an acoustic sensing unit 1, an amplifier 2, signal processing means 3 and computing means 4, wherein the signal processing means 3 are equipped with a circuit for dividing the output signal of the amplifier 2 into spectral ranges and determining a characteristic value and the average value for each range and the ratio of the characteristic values.

9 Claims, 4 Drawing Figures

METHOD AND APPARATUS FOR CHECKING HETEROGENEOUS TRANSFORMATION PROCESS OF DIFFUSING KINETICS IN TURBULENT LIQUID FLOW

BACKGROUND OF THE INVENTION

The invention relates to a method of and an apparatus for checking a heterogeneous transformation process of diffusion kinetics taking place in a turbulent flow of a liquid.

Many processes in different technical fields concern a heterogeneous transformation process which takes place in a liquid. The chemical and physicochemical transformation processes taking place on certain surfaces, e.g. on limiting surfaces of different phases, e.g. in systems comprising a liquid dispersive phase and a diespergated liquid, gaseous or solid phase, on catalytical surfaces, electrodes immersed into liquid or on the wall of a liquid vessel are generally classified as heterogeneous transformation processer.

The invention relates to checking such heterogeneous transformation processes taking place in liquids, for which the following conditions are satisfied: that the liquid performs a turbulent flow and the process is characterised by diffusion kinetics. The latter means that the rate of the transformation process is determined by the rate of material transport from the inner region of the liquid to the surface being the place of the heterogeneous transformation or from this surface to the inner region of the liquid.

For checking the heterogeneous transformation processes taking place in liquids the direct methods have become the most popular. The essence of these methods lies in sampling and in aftergoing chemical or physicochemical analyses of the samples. These methods doubtless ensure the accuracy required by the technical praxis, however, on their basis the real-time intervention or control is practically impossible: in fast changing industrial conditions the direct methods can generally not serve for solving regulation problems. Sometimes sampling is difficult to realise and especially in processes wherein it could be performed only on the condition of stopping the entire process. Another special problem is to be seen in the analysis of components present in small quantities. In this case one sample is less than enough: the contents determined for different samples can differ from one another in a wide range comprising the correct value. Therefore the analysis can rely only a higher number of samples for obtaining an average value which is the better approach of the correct value the higher is the number of samples analyzed.

Another group of solutions which have become known consists of indirect methods, wherein the rate or development of the transformation process can be checked on the basis of measuring parameters depending on the concentration, as pressure, temperature, colour, sound, etc. The known methods ensure the required information promptly, but the accuracy or reliability thereof is not as high as desired for realising a control or regulation loop. In steel production a method has been known for carrying out intervention in an oxygen converter process (Baptizmanski. V. I. et al. IVUZ, Tchornaya Metallurgiya, 1982 No. 2, p. 34 to 38) which is based on an acoustic principle. The essence of this method is following the sound effect and exactly the acoustic pressure level during blowing oxygen into the molten steel bath. According to the recognition shown by the authors a rush form alteration of the acoustic pressure level is a sign of reaching a high density of the slag covering the molten steel and this density makes stopping the oxygen supply advantageous. By this measure it is possible to avoid development of harmful secondary processes, however it is impossible to obtain information on the basis of which data could be gained about the alteration of the carbon content of the steel bath.

SUMMARY OF THE INVENTION

The object of the invention is to create a method and an apparatus whereby sampling can be avoided and concentration data of high reliability can be obtained on heterogeneous transformation processes of diffusion kinetics taking place in a turbulent flow of a liquid, wherein an indirect way of measurement should be applied.

The invention is based on the recognition that the bubbles always present in a turbulent flow of a liquid (bubbles of steam or gas, cavitation bubbles) cause by their oscillation a liquid sound the spectral composition of which remains in a well-defined connection with the turbulent diffusion coefficient characterizing the transformation process. The increasing values of the turbulent diffusion coefficient $D_{turb}$ during the turbulent flow involve a characteristic change of the continuous spectrum of the liquid sound: in the frequency range really covered by the spectrum the ratio of energy contents (effective values) assigned to the frequency values higher than a determined level to the energy contents (effective values) to the lower frequency range. This means the higher is the turbulent diffusion coefficient $D_{turb}$ the higher are the amplitudes of the components of higher frequency in the spectrum of the liquid sound in comparison to the components of lower frequency. According to the recognition there exists a time function $R(t)$ determined in relation to the timely changing spectrum which is in a monotonous functional connection with the turbulent diffusion coefficient $D_{turb}$. In making use of the recognition it is very advantageous that in case of heterogeneous transformation processes of diffusion kinetics taking place in a turbulent flow of a liquid the characteristic actual concentration values can be computed in a known way on the basis of the actual values of the turbulent diffusion coefficient. In order to do it the following data have to be known: the concentration at the beginning, the dependency of the magnitude of the surface giving place the transformation on time and/or concentration if the surface is not stable, and in case of transformation with equilibrium the data concerning the equilibrium concentration, further the number value of the constant present in the rate equation of the transformation.

The aim of invention is to create a method of and an apparatus for real-time checking a heterogeneous transformation process of diffusion kinetics taking place in a turbulent flow of a liquid, wherein the method and appratus are based on the recognition as shown above, on the analysis of the sound effects associated with the turbulent flow. Making use of the concentration values at the beginning and the data of active interventions applied to the transformation process, e.g. supplying active substances, etc., the invention should ensure the real-time checking of the processes of the mentioned kind by detecting the sound effects.

In order to reach the object set a method and an apparatus have been created. The essence of the invention lies in applying the steps of detecting an oscillation or vibration process of acoustic frequency caused by oscillations of steam and/or gas bubbles present in the turbulent flow of liquid, producing an electric signal reflecting the spectral composition of the detected signal and forming therefrom a measure signal reflecting the relative instantaneous value of the turbulent diffusion coefficient of the flowing liquid, for indirect real-time checking the transformation.

For detecting a microphone or a solid state sound meter can be used. Instead of direct detecting it is advantageous to measure the vibration, the solid state sound effect when the frequency range of the liquid sound is wider than the range of the audible sounds and it is necessary in case of placing the turbulent flowing liquid in a vacuum because of the want of a gaseous atmosphere transmitting the oscillations determining the sound.

The signal/noise ratio determining the effectiveness of the detection can be improved by means of bubbles produced in an additional process, e.g., by means of surface-active substances or a pulver of a solid body vapouring in the temperature of the liquid or by blowing a gas into the liquid.

The measure signal can be produced by different methods from the detected signal. The main feature of the measure signal is that it should reflect the spectral composition of the detected signal. One possibility lies in selecting a reference frequency and to divide thereby the spectrum into two parts. The next step is to determine the effective value or average value assigned to one of the mentioned parts and to the entire spectrum or to both mentioned parts and to divide the two values with one another. Generally the value determined for the spectral range lying over the reference frequency is divided by the value determined for the entire spectrum or the other range. According to the recognition shown above the higher ratio means the higher turbulent diffusion coefficient $D_{turb}$.

In a further advantageous embodiment of the method according to the invention the detected signal undergoes spectral transformation before determining the effective or average value. This operation can include noise filtration and the essence thereof lies in modification of the amplitudes in one or more spectral ranges, if required, eventually by deleting some of these ranges. The spectral transformation can be carried out by a series of narrow band filters, a spectral analyzer or a computer connected to an analogue-to-digital converter, etc.

The object set is reached also by an apparatus, capable of carrying out the method shown above, comprising a series member including an acoustic sensing unit, an amplifier, signal processing means and computing means, wherein the signal processing means are equipped with a circuit for dividing the output signal of the amplifier into spectral ranges and determining an effective or average value for each range and the ratio of the determined values.

The signal processing means comprise in an advantageous embodiment a circuit arrangement whereby the output signal of the amplifier can be spectrally transformed.

In the signal processing means of the apparatus according to the invention for carrying out the operation of determining it is advantageous to use input filter means, as a series of narrow band filters or a system of low pass and high pass filters, one or more multiplying units if required, summation means and elements for determining effective or average value arranged in two series members, wherein the outputs of the series members are connected to a dividing unit producing the measure signal identified with the time function R(t). The multiplying units can take part in spectral transformation operations, too.

It is advantageous to equip the computing means with inputs for forwarding constants, calibration and real-time data.

The method and the apparatus according to the invention render possible the real-time checking of heterogeneous transformation processes of diffusion kinetics taking place in a turbulent flow of a liquid and even of liquids not available for direct investigation. Therefore it is very advantageous for use in regulation processes needed in steel production, for detecting the sulphur content of raw iron, and for starting regulation and intervention operations for reaching a sulphur content in a prescribed range.

BRIEF DESCRIPTION OF THE DRAWINGS

The invention will be described in more detail by way of examples and with reference to preferred embodiments and realisations illustrated in the drawings, wherein.

DESCRIPTION OF THE PREFERRED EMBODIMENTS

Figure 1:
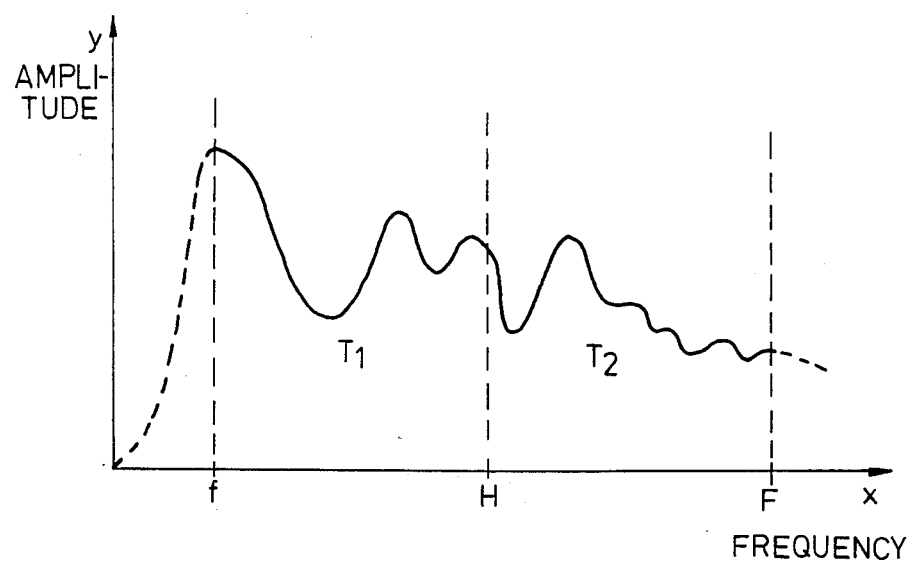
FIG. 1 shows a possible form of a signal processed during realisation of the process according to the invention.

The method according to the invention can be used in an especially advantageous manner during steel production wherein the steel is arranged in a vessel equipped with an inductive mixer. The object set is for example the determination of the optimal time moment of casting and in order to reach it the following of the process of solving an alloying material supplied in pulverized form to the vessel comprising the steel is in turbulent flow. The problem is important because the casting operation can be started at a level of e.g. 99% of solving. The dissolution is a process of diffusion kinetics. A solid state sound meter arranged on the cover element of the vessel carrying the steel detects the sound effects associated with the flow. The effects are measured in the spectral range from 0 up to 16 kHz. In the processing the first step is to exclude from the spectrum the high level noises caused by the current transformer of the induction mixer with maximal amplitude at 50 Hz. These noises with frequency up to 100 Hz attenuate the useful signals. Therefore it is advantageous to eliminate the frequency range from 0 to 100 Hz by means of filters. In a determined time moment a function $y=y(x)$ shown in FIG. 1 can be obtained wherein y means the amplitude and x the frequency. In the FIG. 1 f = 100 Hz is the lower limit of the analysis of the spectrum, F = 16 kHz gives the upper limit and H = 5 kHz the reference frequency thereof. By the reference frequency H=5 kHz the spectrum is divided into two parts $T_1$ and $T_2$. The essence of the proposed method lies in the analysis of functions $y=y(x,t_i)$ determined in time moments $t_i$, and in evaluating the changes following from the analysis. One possibility of analysis is e.g. the determination of an effective value $I_1$ reflecting the spectrum part $T_1$ of the frequency range from 100 Hz to 5 kHz and another efrective value $I_2$ reflecting the full frequency range of analysis, i.e. the spectrum from 100 Hz to 16 kHz. The ratio $I_1/I_2$ of the two effective values gives the measuring signal representing the moment value of the time R(t). Because a transfer function was previously determined by means of preparatory measurements the momentary value of the turbulent diffusion coefficient $D_{turb}$ can be computed. On the basis of this value, the time moment of supplying and the supplied quantity the characteristic concentration showing the development of the dissolution process can be followed.

Another possibility is the determination of the time function R(t) on the basis of an effective or average value $I_3$, by following the values of the ratio $I_3/I_2$, wherein the effective or average value $I_2$ is given above and $I_3$ is determined with a function $y(x,t_i).z(x)$, wherein $z(x)$ is means a spectrum transformation function: for example a monotonous increasing function of the variable x. An appropriate example thereof is the function of the integer part of the ratio x/1000 multipled by 1000. This step is practically a spectrum transformation. By means of the mentioned function z(x) it is possible to eliminate the influence of the amplitudes with frequency lower than 1000 Hz, and the increasing amplitude means increasing influence.

The intensity of the acoustic effect can be increased by artificially producing bubbles in the liquid flowing in a turbulent stream. The bubbles can be produced by a pulverised solid material vapourised in the temperature of the liquid, by a surface-active material or by an appropriate gas blown in, wherein, of course, a material should be selected which cannot affect in a disadvantageous way the process. Other methods can be used, too.

Figure 2:
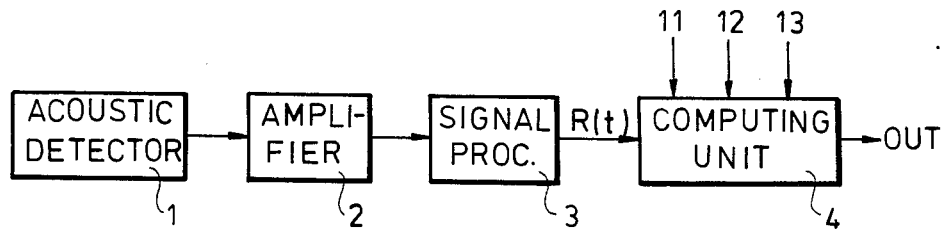
FIG. 2 is a block diagram of the apparatus according to the invention.

The apparatus as proposed by the invention (FIG. 2) is capable of realising the method shown above and generally of real-time checking heterogeneous transformation processes of diffusion kinetics taking place in a turbulent flow of a liquid. The apparatus comprises a series path including an acoustic sensing unit 1 for following the acoustic or sound effect in the turbulent flow of the liquid, an amplifier 2, signal processing means 3 receiving the amplified signal and computing means 4 producing an output signal on the basis of the processed signal. The computing means 4 can be equipped with inputs 11, 12, 13 for forwarding the characteristic constant and real-time data of the process and calibration data.

Of course, the signal processing means 3 and the computing means 4 can form together a computer with appropriate program, and the output signal of the computing means 4 is generally forwarded to a special unit of well-known construction for controlling and/or checking the process to be detected, e.g. for supplying active materials, altering the intensity of mixing etc.

Figure 3:
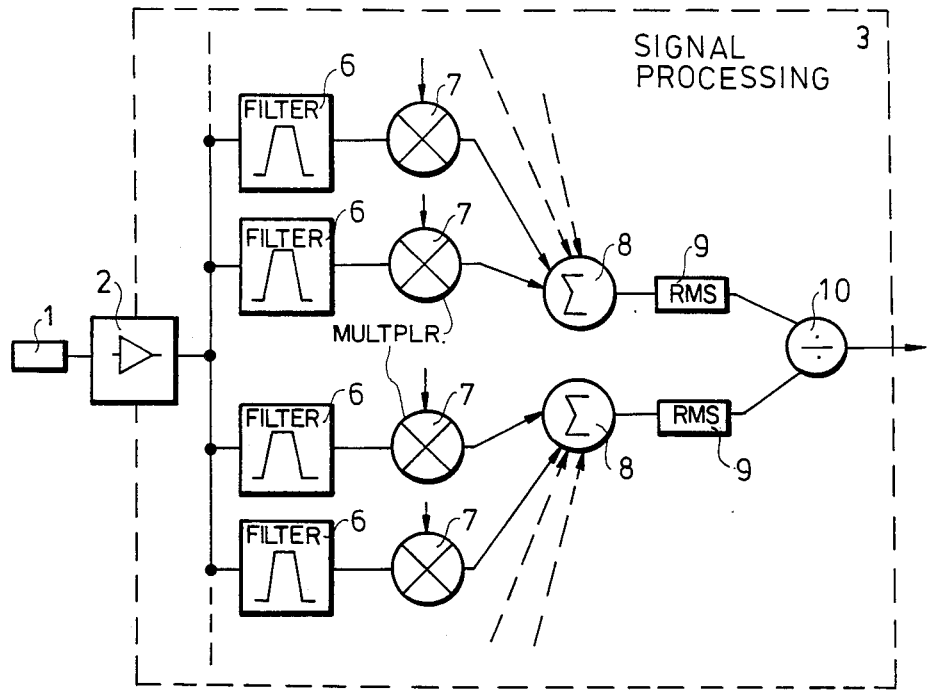
FIG. 3 shows a preferred embodiment of a circuit used in the signal processing means of the apparatus according to the invention.
Figure 4:
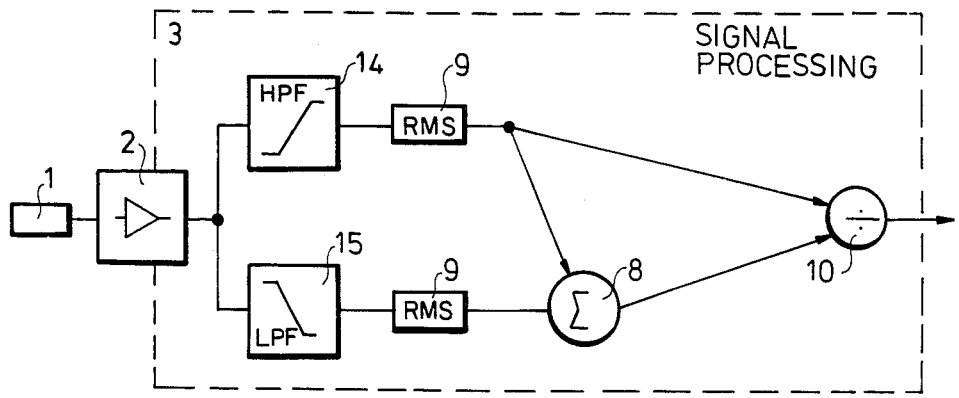
FIG. 4 shows a further preferred embodiment of a circuit used in the signal processing means of the apparatus according to the invention.

The signal processing means 3 comprise a circuit, whereby the output signal of the amplifier 2 can be processed according to the requirement the processing should ensure information about the process detected by the sensing unit 1. An appropriate circuit arrangement can be described in the following manner with reference also to the operation:

The output signal of the amplifier 2 corresponding to the signals produced by the sensing unit 1 is forward to narrow band filters 6 (FIG. 3) arranged in parallel, or to a system of a low pass filter 15 and a high pass filter 14 (FIG. 4). The outputs of the filters are connected directly (FIG. 4) or by means of multiplying units 7 (FIG. 3) to summation means 8 and thereover to elements 9 for determining effective values or average values. The mentioned elements are arranged in two series members the outputs of which are connected to a dividing unit 10 producing on its output a measuring signal consisting of the momentary levels giving the time function R(t). By means of the narrow band filters 6 it is possible to eliminate noises of specific frequencies, if required.

The sensing unit 1 can be a microphone or a solid state sound meter, the output signal of which after amplifying is the input signal to be forwarded to the signal processing means 3. The computing means 4 should produce the output signal required for displaying or the desired data and/or for initiating a regulation or control process.

The invention will be better understood on the basis of the following example.

EXAMPLE

In a vessel there is displaced 64 tons of molten steel and this amount of metal should be desulphurized, i.e. the sulphur content thereof has to reach a predetermined range. The object set is solved by blowing in an active material in a stream of an inert gas carrier, over a lance immerged into the liquid.

The molten steel is in a turbulent flow and comprises the cavitation bubbles and the bubbles of the gas carrier, as well. The heterogeneous transformation of diffusion kinetics is a reaction taking place on the surface of dispergated particles present due to the reaction between the active material blown in and the molten metal. Within this transformation process sulphur dissolved in the molten steel enters the dispergated particles and the particles leave in a continuous process the inner space of the molten steel bath. Their surface magnitude remains practically unchanged during this reaction of receiving sulphur.

For producing a measuring signal containing the momentary values of the time function R(t) a direction sensitive microphone was used, the amplified signal of which as an output signal of the amplifier 2 entered a high pass filter 14 with a lower frequency limit of 7 kHz, and another high pass filter not passing the signal parts of frequency lower than 100 Hz. The second filter ensures filtration of noises of low frequency, practically in the range of 50 kHz, present due to the work of a current transformer arranged adjacent to the vessel with molten steel. The outputs of the filters are connected directly to elements 9 for determining effective values and thereafter to the dividing unit 10 producing an analogous signal. This means that the apparatus generates signals of values reflecting the energy contents assigned to the range $T_2$ and the entire spectrum with range $T_1+T_2$ as shown in FIG. 1. The ratio of these values forms the measure signal with momentary values of the time function R(t).

For preparing the checking process the constants appearing in the function connecting the time function R(t) to the turbulent diffusion coefficient $D_{turb}$, i.e. the transfer function of the measurement were determined.

The determination required the investigation of the desulphurizing process in some cases. For this aim the sulphur content of the steel was determined before handling, by samples taken from the furnace before casting, and after it, in the stream of steel flowing to forms, by means of a photometric flame detector. From the denoted values of the time function R(t) produced by the apparatus and the data of photometric analysis it was concluded that in the value range of 0.05 to 0.80 of the time function R(t) the actual sulphur concentration S(t) can be described by the kinetic equation:

$$\frac{dS(t)}{dt} = -0.89 \frac{R(t)}{S(t)E(t)},$$

wherein E(t) is the equilibrium sulphur concentration. The theoretic investigation shows that the equilibrium sulphur concentration can be described by the equation:

$$E(t) = \frac{S_0}{1 + 0{,}0225\ m(t)},$$

wherein $S_O$ is the sulphur concentration before casting and m(t) is the mass of the active material blown into the steel up to moment t of the casting and determined by means of an electronic balance.

The real-time checking of the transformation is carried out in the following way: the signals representing the time function R(t) of the apparatus according to the invention and the signals of apparatus comprising the balance are processed by a microcomputer storing the actual form of the kinetic equation. In short time sequences the actual sulphur concentration S(t) is computed on the basis of the known (from the analysis of the samples) value of the sulphur concentration $S_O$. The analysis of the sample lasts about 20 to 30 minutes and this means that the handling of a steel bath should be started in this time after taking a sample from the furnace. The duration of the checking process is relatively short, from 3 to 10 minutes which depends on the rate of reaching the required sulphur content.

The checking is aimed at producing steel with an acceptable level of sulphur content. It is, however, important for avoiding the use of a high amount of active material not to undergo a prescribed lower level because the low sulphur concentration is also harmful: it starts with increasing intensity a secondary process of dissolving nitrogen from the air with relatively high intensity after eliminating sulphur.

The data obtained by photometric flame analysis of samples taken after handling gave a high proof of the method of invention. The sulfur content of the samples taken at a value of the time function R(t) predetermined by preparatory measurements was equal to those expected on the basis of the samples analyzed previously by flame photometry. The results were proved by 21 measurements carried out by the method and apparatus of the invention compared to the sampling investigations according to the prior art.

The method and apparatus according to the invention render possible real-time checking of a lot of processes by means of relatively simple solutions, without sampling. It is especially advantageous that in case of meeting some conditions, the conditions of Reynolds-analogy, it is possible to determine the values of the turbulent viscosity coefficient and the turbulent thermal conductivity number on the basis of the turbulent diffusion coefficient.

The correct results of measurements can be reached only on the condition of performing checking measurements and computations, sometimes checking during the measurements. The proposed method and apparatus are capable, however, of producing reliable data required in real-time processes and thereby of solving an object not reached before.

From the above description it should be understood that methods and apparatuses equivalent to those shown above as examples will be within the scope of the claimed invention and such methods and apparatuses will work on conditions depending on the field of the application and the given circumstances.

What we claim is:

1. A method of checking a heterogeneous transformation process of diffusion kinetics taking place in a turbulent flow of a liquid, comprising the steps of detecting a vibration process of acoustic frequency caused by oscillations of bubbles present in said turbulent flow of liquid, producing an electric signal reflecting the spectral composition of said detected signal, and forming therefrom a measure signal reflecting the relative instantaneous value of the turbulent diffusion coefficient of said flowing liquid, for indirect real-time checking said transformation.

2. The method as claimed in claim 1, comprising the step of producing bubbles in said liquid in an artificial way.

3. The method as claimed in claim 1, comprising the step of dividing said detected signal into two spectral ranges for producing said electric signal reflecting the spectral composition and determining the ratio of the effective values of said spectral ranges.

4. The method as claimed in claim 1, comprising the step of dividing said detected signal into two spectral ranges for producing said electric signal reflecting the spectral composition and determining the ratio of the value of said spectral ranges.

5. The method as claimed in claim 1, comprising the step of spectral transforming said detected signal before producing said electric signal.

6. An apparatus for checking a heterogeneous transformation process of diffusion kinetics taking place in a turbulent flow of a liquid, comprising a series connected circuit including acoustic sensing means, an amplifier, signal processing means and computing means, wherein said signal processing means are equipped with a circuit for dividing the output signal of said amplifier into spectral ranges and determining a characteristic value selected from the group comprising the effective value and the average value for each range and the ratio of said characteristic values.

7. The apparatus as claimed in claim 6, wherein said signal processing means (3) comprise a circuit for spectral forming said output signal of said amplifier.

8. The apparatus as claimed in claim 6, wherein said computing means comprise inputs for forwarding real-time data, constants and calibration data.

9. The apparatus according to claim 6, in use for real-time controlling a heterogeneous transformation process of diffusion kinetics taking place in a turbulent flow of a liquid.

* * * * *